Figure 4:
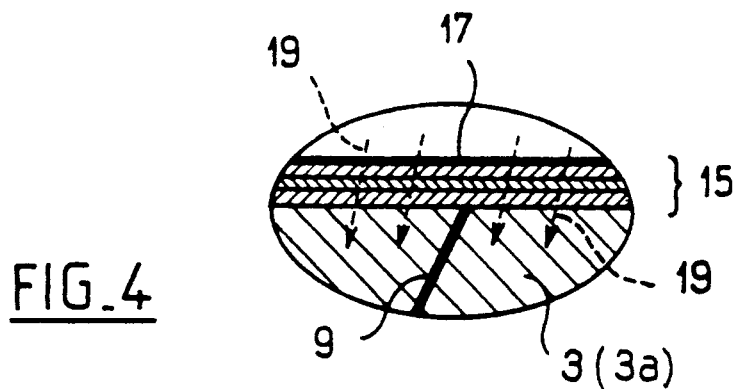

United States Patent
Di Bin et al.

[11] Patent Number: 5,280,172
[45] Date of Patent: Jan. 18, 1994

[54] FIBER OPTIC SENSOR FOR MEASURING GAS

[75] Inventors: Philippe Di Bin, Limoges; Paul Facq, Panazol; Thierry Pichery, Saint Denis, all of France

[73] Assignee: Gaz de France, Paris, France

[21] Appl. No.: 974,625

[22] Filed: Nov. 12, 1992

[30] Foreign Application Priority Data

Nov. 12, 1991 [FR] France ............... 91 13887
Nov. 5, 1992 [EP] European Pat. Off. ....... 92402993.7

[51] Int. Cl.⁵ .......................... H01J 5/16; H01J 40/14
[52] U.S. Cl. ............................ 250/227.21; 385/12
[58] Field of Search .......... 250/227.14, 227.21; 385/12, 124, 125

[56] References Cited

U.S. PATENT DOCUMENTS

| | | | |
|---|---|---|---|
| 4,807,950 | 2/1989 | Glenn et al. | 385/123 |
| 4,834,496 | 5/1989 | Blyler, Jr. et al. | 250/227.18 |
| 4,846,548 | 7/1989 | Klainer | 385/12 |
| 4,878,015 | 10/1989 | Schmidt et al. | 257/414 |
| 4,996,419 | 2/1991 | Morey | 250/227.18 |
| 5,138,153 | 8/1992 | Gergely et al. | 250/227.14 |

FOREIGN PATENT DOCUMENTS

| | | |
|---|---|---|
| 438757 | 12/1990 | European Pat. Off. |
| 438759 | 12/1990 | European Pat. Off. |
| 3723159 | 3/1986 | Fed. Rep. of Germany |
| 8601286 | 2/1986 | World Int. Prop. O. |
| 8700633 | 1/1987 | World Int. Prop. O. |
| 9110156 | 7/1991 | World Int. Prop. O. |

OTHER PUBLICATIONS

Lukosz, et al, "Sensitivity of Integrated Optical Grating and Prism Couplers as (bio)chemical Sensors," Sensor and Actuators, vol. 15, No. 3, Nov. 1988, pp. 273-284.

*Primary Examiner*—David C. Nelms
*Assistant Examiner*—Stephone B. Allen
*Attorney, Agent, or Firm*—Pollock, VandeSande & Priddy

[57] ABSTRACT

This is a system of fibre optic sensors comprising at least one such fibre for measuring a physical or chemical parameter sensitive to the change in an environment (E) within which the sensor is placed, the said fibre comprising a cladding (3), a core (5) surrounded by this cladding, an axis (7) with a length in the direction of this axis, and, locally along its parts (9) with variations in optical thickness forming an optical diffraction grating (10), at least one part of the cladding (3) comprising in its composition an active material whose optical properties vary as a function of the change in the said parameter (P) within the environment where the sensor is placed. The active material may be a heteropolysiloxane.

10 Claims, 2 Drawing Sheets

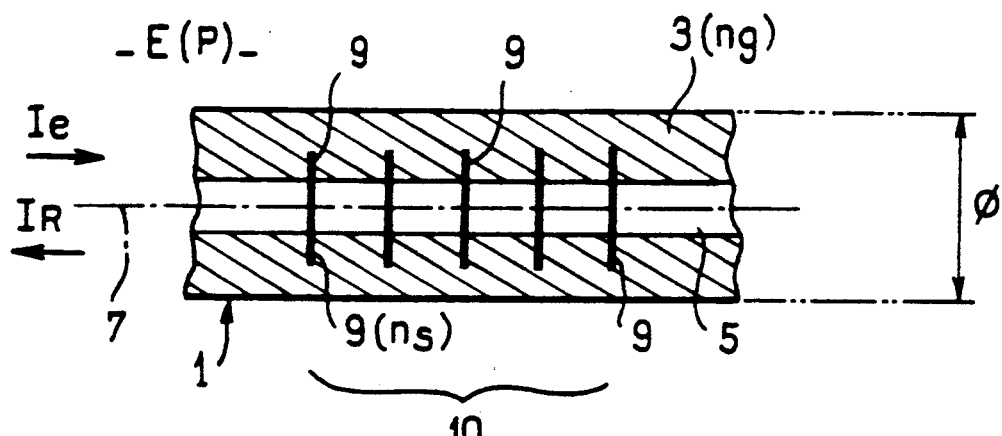
FIG_1
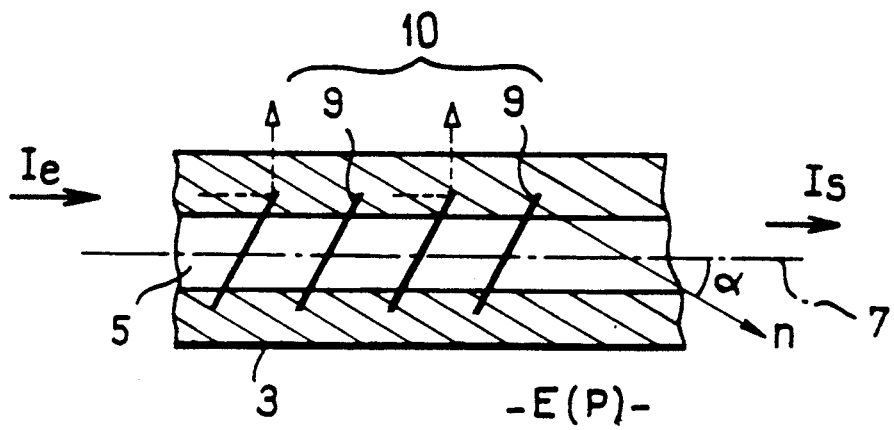
FIG_2
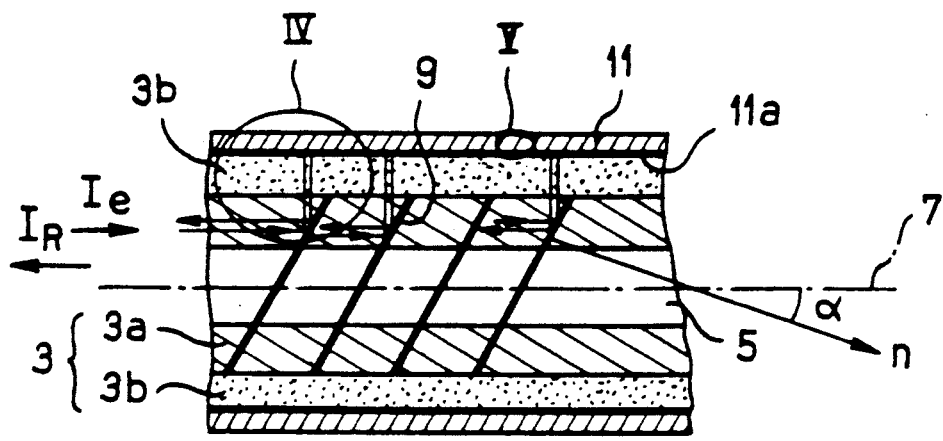
FIG_3

FIBER OPTIC SENSOR FOR MEASURING GAS

The invention relates to a sensor, and more particularly an intrinsic fibre optic sensor. One favoured and more particularly envisaged application of this sensor is as a gas sensor. However, the definition of the sensor of the invention allows it equally to be used as, for example, a temperature sensor, or even as a sensor of any physical or chemical parameter which would be sensitive to the change in the environment within which the sensor will be placed.

In particular in the field of optical gas detectors or sensors, it is currently known that their advantages allow reduced maintenance and operation in an oxygen-free atmosphere, their selectivity and their resistance to the corrosive gases having furthermore contributed to their success in a number of high-technology applications.

Completely optical apparatuses, and more particularly fibre optic sensors, with single or networked optical fibres, have in addition the following advantages: intrinsic electrical safety (no requirement for electrical insulation), possibility of distributed measurements (combination in series, for example with continuous sensitivity), insensitivity to electromagnetical perturbations, reduced weight and bulk.

With such sensors, the optical detection in particular of a gas is normally performed in an open or closed cell, through which a light ray of determined wavelength interacting with the gas to be detected passes, in accordance with the principle of spectroscopic absorption. The difference in intensity between the input light signal and the output light signal of the cell gives an indication of the concentration of this gas.

Other research relates finally to fibre optic chemical sensors which do not use a detection cell. Thus Patent EP-A-0275275 gives an example of a fibre optic sensor for detecting a physical or chemical parameter, or alternatively a substance, using the combination of at least one selective layer disposed on a surface of the fibre and an optical diffraction grating with which this fibre is provided, the selective layer comprising, in its composition, an optically conducting organic material whose optical properties are sensitive to the said substance or to the said parameter, in order consequently to modify, by the intermediary of an optical diffraction grating, the optical properties of a wave propagating in the fibre.

However, this document EP-A-0275275 gives no indication as to the structure of the fibre; it is simply specified that it comprises an annular Bragg grating.

Difficulties in implementing this type of sensor remain, in particular when the fibre is made with a central part or core forming a waveguide, this core being surrounded by at least one optically conducting cladding. In practice, these difficulties are in particular linked to the low proportion of light normally propagating outside the core of the fibre (the evanescent field proportion hitherto often being less than approximately or to the increased fragility of the fibre when it 1%), or to the increased fragility of the fibre when it is treated so as to have a larger evanescent field (because of a reduction in the diameter of the fibre, and of the core in particular).

Furthermore, the selectivity or sensitivity of existing sensors is not always suitable, and it is often tricky to vary it.

Against this background, the invention provides a fibre optic sensor, of the general type of that in Patent EP-A-0275275, in which the fibre comprises a waveguide core surrounded by an optically conducting cladding, the selective layer occupying at least one external portion of the said cladding and surrounding, at the position of the diffraction grating, an internal optically neutral portion of this cladding which comes into contact with the core.

In this way it will be possible to obtain a sensor ensuring a compromise (which may change) between the resilience of the fibre (mechanical strength of the core) and the sensitivity of the sensor (linked to the thickness of the selective layer). Alteration of this selectivity will thus be possible, by adapting it as a function of the types of detection to be performed (temperature measurement, measuring the gas content of an atmosphere, etc.).

The composition of the optical diffraction grating may be obtained by various means.

It would for example be possible to choose to make the grating with strata at the optical cladding. This option would require deposition of a material rather than making these strata optically. Research into this is in progress.

However, the solution which the invention more particularly consists in making this grating as a Bragg grating, by creating it optically, for example by optical pumping. For this purpose the fibre (and in particular its core) will be exposed to an interference field resulting from the mutual interference of two ultraviolet radiation beams directed simultaneously towards the fibre with different acute angles of incidence with respect to the longitudinal axis of the fibre, so that periodic variations in the refractive index appear, at least in this core. The interference field will thus have, at the engraved grating, fringes or strata from each other and will be propagated transversely in the fibre with an alteration (which can be permanent if the intensity of the radiation is so adapted) i refractive index of the zone of creation of these strata, in correspondence with the interference field.

Given that there has recently been interest in using fibre optical components which allow light to be injected and/or extracted, if necessary selectively (see in particular FR-A-2,674,639 or the corresponding American Application U.S. Pat. No. 07/858,009 of Mar. 26 1992), an additional characteristic of the invention advantageously provides for these periodic variations in the local refractive index to be engraved in order to be substantially parallel to each other and have a normal which makes an angle $\alpha$ with the axis of the fibre, such that $0° < \alpha < 90°$.

In this case, in order to make the fibre operate in reflection, the cladding will then be preferentially surrounded by a mirror having a reflecting concave internal surface, directed to the fibre, in order to return to it the light wave with which it will have been illuminated.

Figure 5:
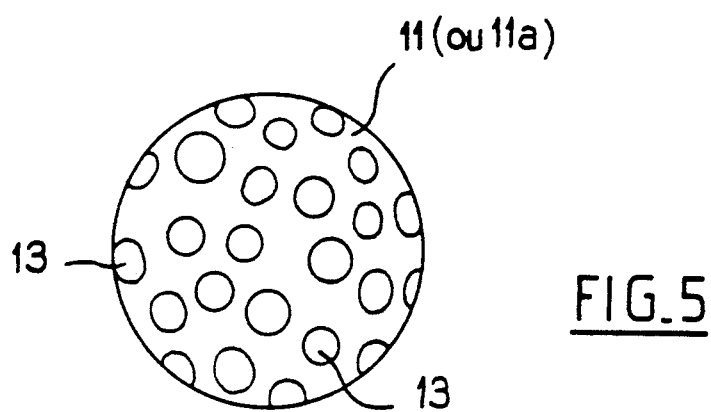
Figure 6:
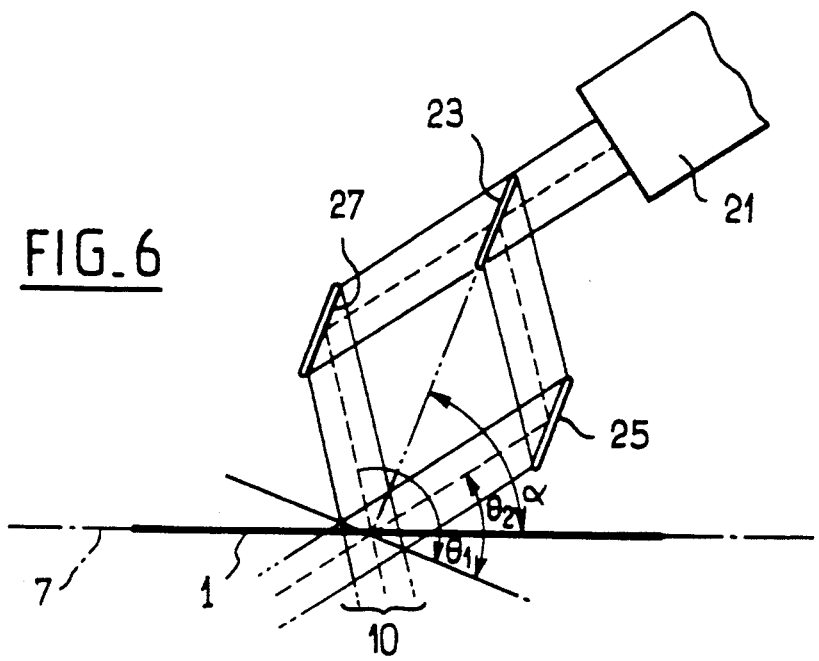

A more detailed description of the invention will now be given by way of non-limiting example, and with reference to the attached accompanying diagrams in which:

FIG. 1 is a view in longitudinal section of a first type of sensor which can be used in accordance with the invention, FIG. 2 is a view which is comparable with that of FIG. 1 showing a first embodiment, FIG. 3 is, also along a view in section identical to that in FIG. 1, a representation of a second embodiment, FIG. 4 is one embodiment of the cladding, solely as a detailed view corresponding to the part labelled IV in FIG. 3, FIG. 5 is an enlarged plan view showing one embodiment of construction of the mirror in particular in FIG. 3 according to the detail V, and FIG. 6 shows one way of optically creating the striae.

Each of the first three figures therefore illustrates the principle of an intrinsic fibre optic sensor, the fibre being monomode or multimode.

The following description will be limited, by way of example and solely for clarity of explanation, to the case of a fluid sensor such as a gas sensor.

Each sensor illustrated comprises, here on the basis of only one optical fibre, an optical cladding 3, which is normally transparent, surrounding a transparent core 5, forming a waveguide and extending longitudinally along an axis 7 in order locally to include parts 9 having variations in refractive index (or optical thickness) thus forming an optical diffraction grating.

It will be recalled that the optical thickness $\delta$ of an optically homogeneous (possibly elementary) sheet of thickness e and of refractive index n is such that: $\delta = n \times e$.

For such a fibre to constitute an intrinsic sensor, at least a part of the optically conducting cladding 3, or even the parts 9 with variation in refractive index, comprises in its composition an organic material which is active with respect to the substance to be detected and forms a selective layer whose optical properties can thus vary as a function of the change in the parameter or in the substance P (in this case the gas content), within the environment E in which the sensor is placed.

In the examples illustrated, the aforementioned parts with variation in refractive index are here constituted by zones or strata which are flat and parallel to each other and periodic. These strata preferentially extend into the core 5 and can continue into the optically neutral part of the cladding.

Such optical diffraction gratings are known in the literature by the name Bragg Grating. The optical fibre described in the aforementioned application FR-A-2674639 is a good example of this, the base structure of this fibre being moreover quite usable within the scope of the invention.

For any definition relating to these diffraction (or scattering) gratings, reference may if necessary be made to the "Dictionary of Scientific and Technical Terms", McGraw-Hill, pages 250 and 825 (see "Grating") or to the "dictionnaire de physique" [Dictionary of Physics] by E. Levy (Presse universitaire de France), pages 109 and 685-686.

In order to create the strata 9 grating, optical means are used, starting with a laser source 21 (such as a laser diode) in order to transmit to the fibre, transversely to its axis, an ultraviolet beam which will be separated into two waves which will be made to converge via two mirrors 25, 27, at a certain angle of incidence ($\theta 1$ or $\theta 2$), towards the fibre (see FIG. 6), as proposed (for the grating) in U.S. Pat. No. 4,807,950 or alternatively in U.S. Pat. No. 4,867,522.

As regards the active organic material, provision may be in particular for using a heteropolysiloxane of chemical formula

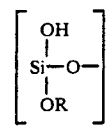

with in particular R being $CH_3$ or $C_2H_5$, this material being able to be deposited in a thin film (of a few microns).

In order to ensure resilience of the assembly, the fibre will preferentially furthermore be coated with one or more mechanical claddings (for example made of Kevlar ®). So as not to complicate the figures further, no mechanical cladding has however been represented.

After this overall presentation, we shall now address ourselves to each figure independently.

It should first of all be noted that in FIG. 1 the strata 9 of the Bragg grating are here made from the said active material so as to be capable of absorbing the gas to be detected whilst having optical characteristics, more particularly reflective properties, which are dependent on this gas concentration.

In the application adopted, the active material constituting these strata will advantageously have a refractive index $n_s$ near the refractive index $n_g$ of the cladding 3 in the absence of gas, the value of $n_s$ moving away from $n_s$ when the gas content in the active material increases.

The Bragg grating, which is almost transparent in the absence of gas, will therefore appear after the gas has been absorbed.

The optical cladding 3 may be made over part of its thickness from a base of the said active material. This being so, it may in any case, like the external protected mechanical cladding, be made of a "porous" or permeable material which allows the gas to be detected to penetrate laterally into the sensor, and the fibre may be made with a core and a cladding based on the same material, the difference in refractive indices existing between them being obtainable, by structural means, by doping the base material of the cladding (normally silica) with a metal oxide (such as germanium oxide $GeO_2$).

In FIG. 1 it will be noticed that the strata 9 which are parallel to each other and periodic are inclined with respect to the axis 7 of the fibre with their normal parallel to this axis. In other words, the strata are therefore perpendicular to the axis 7.

Thus the grating adopted will operate in reflection.

Its principle of use will be the following, irrespective of whether a single fibre or a set of sensors placed end-to-end in series is involved.

After having manufactured the strata 9 made based on the said active material embedded periodically in the fibre, so that these strata can have at least two states with different optical characteristics in the presence and absence of gas, there will be transmitted axially to the fibre in question, from one of its ends, an incident luminous intensity $I_e$ having at least one wavelength corresponding to a resonant wavelength $\lambda_r$ of the optical grating in order for the latter to reflect light having the wavelength $\lambda_r$.

At the same time, the luminous intensity $I_r$ reflected by the fibre at this wavelength $\lambda_r$ will be measured.

The luminous intensities $I_e$ and $I_r$ will next be compared, the ratio between them (in general $I_r/I_e$) being representative of the variation in the parameter P analyzed, and therefore in this case of the presence of the gas to be detected, and even of its concentration, inasmuch as the reflected intensity $I_r$ will increase with the gas concentration.

The example of FIG. 2 differs from that of FIG. 1 essentially in that here the strata 9 of the optical grating are disposed with their normal inclined by an angle $\alpha$ with respect to the axis 7 of the fibre, such that $0° < \alpha < 90°$.

In this case therefore, instead of measuring the reflected luminous intensity, rather the output intensity $I_s$ will be measured, at the opposite end of the fibre, after the light has passed axially through the sensor in question over the whole of its length.

Further, in order to be able to perform these measurements, an incident luminous intensity $I_e$ will be transmitted axially to this fibre with at least one predetermined wavelength chosen in order to make the strata 9 appear as a function of their chromatic signature, these representing, taking account of the composition of the optical grating decided upon, quasiselective absorption.

In this case of course, the more the gas concentration increases in the sensor, the more the intensity $I_s$ decreases, if the incident intensity $I_e$ is taken to be constant, the reflective properties of the strata increasing as does the difference between the refractive indices $n_s$ of the latter and $n_g$ of the cladding 3.

Let us now consider the case of FIG. 3, noting that the optical fibre is here supplemented over at least a part of the periphery of the cladding by a cylindrical mirror 11 of circular cross-section whose purpose will be better understood hereinbelow, the cladding itself here being "divided" into an internal part 3a, adjacent to the core 5 and made of an "inactive" optically neutral material, that is to say one which is not sensitive to the gas to be detected (for example made of doped silica) and an external active part 3b (in particular heterpolysiloxane) which surrounds it, at least at the strata 9, and whose properties of variation in transparency as a function of the gas content will essentially be used. By way of example, for a fibre having a core with a diameter of the order of a few microns, or even a few tens of microns, the radial thickness of the layer 3a can also be a few microns, in general less than 10 microns. A thickness of a few tenths of microns may even be envisaged. The thickness of the selective layer 3b can be a few microns.

As regards the mirror, its reflecting concave internal surface 11a which comes into contact with the external surface of the selective layer 3b can for example be obtained by deposition of a thin layer of a material such as gold, silver or aluminium.

As illustrated in FIG. 5, the mirror 11 in its entirety will advantageously have, at least opposite the grating 10, a lacunary structure with orifices 13 in order to allow the substance to be detected to pass through it. A material will thus be used which is porous to this substance and has holes 13 whose sizes are preferably markedly less than the wavelength of the signal transmitted in the fibre (for example $\lambda/10$).

The cladding 3 may also have been made from an inactive material and surrounded, as in FIG. 5, with a multilayer dielectric mirror 15, which is possibly porous like the mirror 11 (see arrows 19 in FIG. 4) and the optical thickness of at least the external layer 17 of which varies as a function of the gas content of the environment (E). This being so, the result would have been comparable, the cladding 3 and the internal layers of the mirror 15 then acting as the optically neutral part 3a, and the external layer 17 replacing the selective layer 3b.

As for the optical grating, it will have been noted that its strata 9 are, as in FIG. 2, oriented so that their normal makes an angle $\alpha$ ($0° < \alpha < 90°$) with the axis 7 of the fibre, these strata here stopping at the boundary between the parts 3a and 3b of the cladding.

In order for the sensor to operate efficiently, its grating will resonate substantially around a determined and known wavelength $\lambda_r$.

Once this has been produced, it will be possible to transmit axially into the fibre(s), still at one end, an incident luminous intensity $I_e$ having as its wavelength or as one of its wavelengths the said resonant wavelength $\lambda_r$.

The luminous flux will then be extracted from the fibre by the grating and reflected by the mirror 11 (or 15) in order thus to be reinjected into the fibre in question.

When the gas is present in the active material of the selective layer, and when the waveguide used corresponds to the wavelengths of absorption of the gas, the light present in this material (and therefore in contact with the gas) will thus be absorbed, causing a drop in reflected intensity $I_r$.

Thus, in the presence of gas, the absorption intensity will be a function of the length of the grating 10, of the quantity of gas sensed, and of the thickness of the zone containing the active material.

With such a construction, it will in particular be possible to obtain a selective sensor or a series of selective sensors.

In fact, if the strata 9 are themselves produced with the said active material and when a polychromatic light (for example a white light) is transmitted to the said fibre, the grating will then itself select the resonant wavelength $\lambda_r$ which it will reflect, this wavelength corresponding to the absorption line of the sensed gas, the analysis being performed, as in the case in FIG. 1, by picking up the incident ($I_e$) and reflected ($I_r$) luminous intensities and comparing them.

If conversely the strata of the Bragg grating are not produced based on the active material, a monochromatic light covering the resonant wavelength of this grating as well as the absorption line of the gas to be detected will be transmitted into this fibre, the selectivity being, in this case, performed "on input" by the operator.

In general, as means for measuring the luminous intensities a photomultiplier, a photoconducting detector or a photodiode, possibly an avalanche photodiode will be able to be used. In these four possibilities, the photodiode is the one most commonly used. It is fitted to most reflectometers used for measuring the reflected luminous flux ($I_r$). The incident luminous intensity ($I_e$) is normally supplied by the manufacturer of the apparatus. Its value may in any case be verified by one of the aforementioned measurement means.

Another measurement method could moreover consist in using a known reflectometric method to measure the luminous intensity ($I_r$) reflected by the sensor or series of sensors. For all information relating to such a method, reference may be made in particular to the publication "Opto No. 63 - September/October 1991" relating to optical fibre grating measurements. The following publications will also be informative to the reader: "Principles of Optical Fiber Measurements" (Academic Press Inc., 111 Fifth Avenue, New York)

and "Very High Optical Return-Loss Measurement using the OTDR Technique" (Symposium on Optical Fiber Measurements, Boulder, Colo., Sept. 11-12 1990).

Of course, even if these methods for recording a reflected luminous flux appear attractive, the solution consisting in adopting a fibre structure comparable to those in FIGS. 3 to 5, with or without a mirror and with strata perpendicular to the axis of this fibre, could be selected and does not, in any case, depart in any way from the scope of the invention.

We claim:

1. A fiber optic sensor for detecting a physical parameter or chemical substance, comprising:
    at least one optical fiber section extending along a predetermined axis for passing a light beam of a predetermined intensity therethrough, said fiber section including an axial waveguiding core,
    at least one Bragg diffraction grating region in said optical fiber section, including a plurality of grating elements constituted by periodic refractive index variations substantially parallel to each other in the direction of said axis and having a determined position relative thereto, for redirecting said light beam reaching said grating elements in a direction depending on the position thereof,
    an optically conductive tubular layer concentrically positioned outwardly of said waveguiding core, and
    at least one layer of an optically conductive organic material located at least in said optically conductive tubular layer, said material having predetermined optical transparency and reflexion values which are responsive to said parameter or substance, for modifying the intensity of said redirected light beam reaching said material, as a function of said parameter of substance to be detected.

2. The sensor set forth in claim 1 wherein said grating elements are essentially disposed in said waveguiding core.

3. The sensor set forth in claim 1 wherein said grating elements form acute angles relative to aid optical fiber section axis.

4. The sensor set forth in claim 1 wherein said grating elements are disposed perpendicularly to said optical fiber section axis.

5. The sensor set forth in claim 1 wherein the organic material is a heteropolysiloxane.

6. A fiber optical sensor for detecting a physical parameter or chemical substance therein, comprising:
    at least one optical fiber section extending along a predetermined axis for passing, a light beam of a predetermined intensity therethrough, said fiber section including an axial waveguiding core,
    at least one Bragg diffraction grating region in said optical fiber section, including a plurality of grating elements constituted by periodic refractive index variations substantially parallel to each other in the direction of said axis and having a determined position position relative thereto, for redirecting said light beam reaching said grating elements in a direction depending on the position thereof,
    a tubular cladding concentrically positioned outwardly of said waveguiding core said including,
    (a) an optically neutral conducting tubular layer outwardly surrounding said waveguiding core; and
    (b) an optically selective conductive tubular layer concentrically disposed outwardly of said optically neutral layer and including an optically conductive organic material having predetermined optical transparency and reflexion values which are responsive to said parameter or substance, for modifying the intensity of said redirected light beam reaching said optically selective layer, as a function of said parameter or substance to be detected.

7. The sensor set forth in claim 6 wherein said grating elements are essentially disposed in said waveguiding core.

8. The sensor set forth in claim 6 wherein the cladding is enclosed by a mirror member having a reflecting concave inner surface directed toward the waveguide, thereby reflecting incident light radially inward.

9. The sensor set forth in claim 8 wherein the mirror member is porous to allow passage of the substance to the organic material.

10. The sensor set forth in claim 8 wherein the organic material is a heteropolysiloxane.

* * * * *

UNITED STATES PATENT AND TRADEMARK OFFICE
CERTIFICATE OF CORRECTION

PATENT NO. : 5,280,172
DATED : January 18, 1994
INVENTOR(S) : Philippe Di Bin et al.

It is certified that error appears in the above-indentified patent and that said Letters Patent is hereby corrected as shown below:

Column 7, line 39, after "parameter", replace "of" with --or--.

Column 8, line 6, replace "optical" with --optic--.

Column 8, line 9, replace "passing," with --passing--.

Column 8, line 17, delete "position" (second occurrence).

Column 8, line 22, after "core", replace "said" with --and--.

Column 8, line 22, replace "including," with --including--.

Signed and Sealed this

Eleventh Day of October, 1994

Attest:

BRUCE LEHMAN

*Attesting Officer*  *Commissioner of Patents and Trademarks*